| United States Patent [19] | [11] Patent Number: 4,797,361 |
| Montenecourt | [45] Date of Patent: Jan. 10, 1989 |

[54] MICROORGANISM AND PROCESS

[75] Inventor: Bland S. Montenecourt, Bloomsbury, N.J.

[73] Assignee: Lehigh University, Bethlehem, Pa.

[21] Appl. No.: 96,766

[22] Filed: Sep. 11, 1987

Related U.S. Application Data

[63] Continuation of Ser. No. 868,168, May 22, 1986, abandoned, which is a continuation of Ser. No. 544,819, Oct. 24, 1983, abandoned.

[51] Int. Cl.$^4$ .................... C12N 9/20; C12N 9/22; C12N 9/26; C12N 9/30; C12N 9/42; C12N 9/58; C12N 1/14; C12N 1/22
[52] U.S. Cl. ..................... 435/198; 435/199; 435/201; 435/203; 435/209; 435/223; 435/252; 435/254; 435/945
[58] Field of Search ............... 435/209, 203, 200, 254, 435/945

[56] References Cited

U.S. PATENT DOCUMENTS

| 3,642,580 | 2/1972 | Ghose | 435/945 X |
| 4,275,163 | 6/1981 | Gallo | 435/209 |
| 4,472,504 | 9/1984 | Gallo | 435/209 |

OTHER PUBLICATIONS

Farkas et al, in Biochimica et Biophysica Acta, vol. 706, pp. 105–110 (1982).

*Primary Examiner*—Thomas G. Wiseman
*Assistant Examiner*—Charles L. Patterson, Jr.
*Attorney, Agent, or Firm*—Ratner & Prestia

[57] ABSTRACT

This invention includes a process for producing and using increased quantities of extracellular glycoprotein (particularly cellulolytic) enzymes by permitting the enzyme-producing microbial strain to undergo a preliminary growth phase, preferably at about 37° C., and then an enzyme-secretion phase. Also included is a specific microbial strain, RL-P37 of *Trichoderma reesei*, which grows well at 37° C. and the cellulasic products thereof.

10 Claims, No Drawings

MICROORGANISM AND PROCESS

This application is a continuation of application Ser. No. 868,168, filed 5/22/86 which is a continuation of application Ser. No. 544,819, filed 10/24/83, both now abandoned.

BACKGROUND OF THE INVENTION

This invention relates to a new microorganism strain, the enzyme products thereof and processes using same, by which biomass, particularly cellulosic biomass, can be broken down into its simpler components.

The energy crisis which began in the early 1970's focused attention on the need to reduce dependence on fossil fuels. This attention was focused, in part, on the conversion of cellulosic biomass to its simpler sugars, which could then be converted to alcohol via the fermentation process.

The hydrolysis of cellulose and other biomass components is achieved by the action of a group of enzymes called cellulases. (T. M. Wood and S. I. McCrea, "The Mechanism of Cellulase Action with Particular Reference to the Cl Component," *Proceedings of Bioconversion of Cellulosic Substances Into Energy, Chemicals and Microbial Protein*, T. K. Ghose, ed., pp. 111–41, Thompson Press (India), Ltd., Fariadabad, Haryana, India (1978)).

The cellulase system of *Trichoderma reesei* (wild strain QM6a and derivatives thereof) is capable of efficiently degrading crystalline cellulose to glucose. That system consists of three different hydrolytic enzymes, endoglucanases (endo-1,4-$\beta$-D glucanase EC 3.2.1.4) which attack cellulose derivatives carboxymethyl cellulose and amorphous cellulose, exoglucanases typified in *Trichoderma reesei* by cellobiohydrolase (1, 4-$\beta$-D glucancellobiohydrolase EC 3.2.1.91) and cellobiase (EC 3.2.1.21). Within the above three enzyme groupings, five to eight electrophoretically distinct endoglucanases have been described (V. Farkas, A. Jalanko and N. Kolarova, "Characterization of Cellulase Complexes From *Trichoderma reesei* QM9414 and Its Mutants by Means of Analytical Isoelectric Focusing in Polyacrylamide Gels," *Biochem. Biophys. Acta.* 706: 105–10 (1982)); these include two immunologically distinct cellobiohydralases (CBH I and CBH II) (L. G. Fagerstam and L. G. Pettersson, "The 1,4-$\beta$-glucan cellobiohydrolases of *Trichoderma reesei* QM9414: A New Type of Cellulolytic Synergism," *FEBS Letters* 119: 97–100 (1980); L. G. Fagerstam and L. G. Pettersson, "The Celluloytic Complex of *Trichoderma reesei* QM9414: An Immunochemical Approach," *FEBS Letters* 98: 363–67 (1979)), and three cellobiases (C. S. Gong, M. R. Ladisch and G. T. Tsao, "Cellobiase From *Trichoderma viride*: Purification, Properties, Kinetics and Mechanism," *Biotechnology Bioengineering*, XIX: 959–98 (1977)).

Previous patents have dealt with the enzymatic conversion of cellulose to fuel, food, and chemicals. For example, U.S. Pat. No. 3,642,580 describes a rapid and complete method of hydrolysis of cellulose into simple sugars employing an enzyme slurry produced from *Trichoderma viride* (reclassified as *Trichoderma reesei* in 1977) QM9123 and a suspension of finely ground cellulose. Similarly, U.S. Pat. No. 4,275,163 discloses MCG77, as a new strain of *Trichoderma reesei*, useful for producing cellulase. The present inventor, with others, has previously disclosed other microbial strains with enhanced cellulolytic enzyme activity, including RUT-NG14, and a screening process that is useful in identifying and selecting microbial strains with enhanced cellulolytic activity. This process also is useful in selecting strains that exhibit less end-product inhibition than unscreened strains.

SUMMARY OF THE INVENTION

One objective of this invention is to provide a microbial strain capable of efficiently producing extracellular glycoprotein enzyme.

Another objective of this invention is to provide a new microbial strain capable of producing enzyme, useful in the hydrolyzation of biomass to its simpler compounds.

Still another objective of this invention is to provide a microbial strain with improved growth characteristics at elevated temperatures, which strain also produces enzyme useful in the hydrolyzation of biomass to its simpler components.

A still further objective of this invention is to provide a microbial strain and a method of utilizing that strain to produce cellulolytic enzymes with enhanced ability to convert cellulosic biomass into its glucose derivatives.

Another objective of this invention is to provide cellulases with enhanced specific activity.

Another objective of this invention is to provide a new microbial strain which is more productive, as compared to related strains heretofore available, with respect to the formation of cellulase.

These and other objects, which will be apparent in the course of the subsequent description of this invention, are met by a new strain of *Trichoderma reesei*, designated RL-P37, the extracellular glycoprotein enzyme product thereof, and methods involving the growth of the RL-P37 culture and subsequent expression from that growth of a biomass converting enzyme, all in the presence of suitable biomass and an inducing substrate.

One significant characteristic of RL-P37 is its enhanced growth rate at elevated temperatures, on the order of 37° C.; this leads to enhanced productivity of the extracellular gylcoprotein enzyme because the RL-P37 in the process is permitted first to undergo an optimal growth phase, at elevated temperatures (on the order of 37° C.), with a concomitant reduction in the amount of cooling water which might otherwise be required to maintain the culture at the optimum growth temperatures (on the order of 28° C. for prior strains). The process temperature is then lowered to about 28° C. for optimum enzyme expression.

Preferably, RL-P37 is utilized in a method in which the inducing substrate and biomass to be converted are cellulosic material, most preferably steam exploded wood. The cellulases of this process are characteristically different and of higher specific activity, as compared to the cellulases of closely related strains of *Trichoderma reesei*.

For a better understanding of this invention, reference may be made to the detailed description thereof which follows and to the appended claims.

DETAILED DESCRIPTION OF THE INVENTION

The microorganism of this invention, *Trichoderma reesei* RL-P37, NRRL No. 15709 is available as a biologically pure culture from the permanent collection of the Northern Regional Research Laboratory, U.S. Department of Agriculture, Peoria, Ill., U.S.A. This deposit was submitted by Dr. Bland S. Montenecourt and was received in the above-referenced Laboratory on Oct. 21, 1983. Two essential characteristics of this microorganism are (1) its ability to grow or be cultured effectively at elevated temperature (on the order of 37° C., for example) and (2) its ability to produce cellulase having higher specific activity than that of related strains of *Trichoderma reesei*. Accordingly, progeny of RL-P37 having these characteristics, that is mutants and genetically engineered modifications or microbiologically modified forms thereof, as well as non-mutated cultures thereof, are also considered part of the present invention.

It is known that cellulase and other extracellular glycoprotein enzymes may be produced from *Trichoderma reesei* by the culture of the seed microorganism in a biomass liquid culture, including mineral salts, an organic nitrogen source, and a cellulosic biomass as the inducing substrate. Enzymes other than cellulases which may be produced in this manner include other carbohydrases, e.g., laminarinase (using $\beta$1-3 glucans as the inducing substrate); amylase (using $\alpha$1-6, or $\alpha$1-4 glucans (starch) as the inducing substrate); or hemicellulose xylans (xylanase) (using $\beta$1-4 xylans as the inducing substrate.) Other extracellular glycoprotein enzymes may also be produced. These include proteases, lipases and nucleases.

In any of these processes regardless of the glycoprotein enzyme being produced, a higher productivity would be expected utilizing the microbial strain of this invention because of its enhanced growth of the seed microorganism at elevated temperature. This is characteristic of the microorganism of this invention and this characteristic facilitates higher productivity of the glycoprotein enzyme through sequential temperature manipulation of the process wherein the culture is first permitted to grow rapidly at the optimum growth temperature of the microorganism (typically an elevated temperature on the order of 37° C. in the case of RL-P37 itself) and, after a period of time (on the order of 24 hours in the case of the preferred method of the present invention) reducing the temperature to about 28° C. for optimal expression of the glycoprotein enzyme from the microorganism culture.

As compared to the microorganism of the present invention, previously known and related microbial strains that produce cellulase enzymes, for example, grow most rapidly and produce the greatest amount of the cellulase enzyme complex at 28° C. Industrial batch processing of biomass to hydrolytic end products using such microorganisms would require a large amount of cooling water in order to maintain the batch at the optimal temperature in view of the exothermic reaction involved in culture growth.

The preferred method of use of the microorganism of the present invention is in the enzymatic hydrolysis of cellulose, particularly a cellulosic biomass comprising steam exploded wood.

Enzymatic hydrolysis of cellulose by a cellulase complex offers certain advantages over chemical hydrolysis of cellulose, since enzymes are reusable, energy sparing, non-polluting and promote high conversion efficiencies without undesirable side products. Unfortunately, the commercial feasibility of such enzymatic hydrolysis has been hampered by the high cost of the microbially produced cellulase complex and the low yields of glucose.

An example of how this invention may increase the efficiency of industrial biomass conversion follows. The typical fermentation takes 100 to 120 hours. Previously it was necessary to maintain the batch temperature at 28° C. throughout the fermentation, thus using large quantities of cooling water. The laboratory tests of this invention indicate that the process of this invention will allow the batch temperature to be maintained at 37° to 40° C. during approximately the first 24 hours of growth. This is the time in which the growth of the microorganism generates the maximum heat of fermentatin and which previously required the greatest amounts of cooling water to maintain the 28° C. temperature. The temperature is then shifted to 28° C. for the balance of the fermentation.

The microbial strain of this invention, RL-P37, was obtained from its parent Rut-NG14, by mutagenesis with ultraviolet light and incubation on a substrate of 2.5% acid swollen cellulose and 0.5% 2-deoxyglucose. The strain Rut-NG14 was obtained from its parent Rut-M7, by mutagenesis with nitrosoguanidine and incubation on a substrate of 1% acid swollen cellulose and 5% glycerol. The strain Rut-M7 was obtained from its parent *Trichoderma reesei* QM6a (wild type) by mutagenesis with ultraviolet light and incubation on a substrate of 0.5% acid swollen cellulose and 5% glycerol.

RL-P37 differs from its immediate parent, NG-14, and its ultimate wild parent, OM6a, inter alia, in that it is catabolite repression-resistant. Thus, unlike QM6a, and to a greater extent than NG-14, enzyme production using RL-P37 can be conducted in cornsteep liquor and is not repressed by other readily metabolizable substrates, such as glycerol.

In order to characterize the properties of *Trichoderma reesei* RL-P37 a series of controlled fermentations using either proteose peptone or cornsteep liquor as a source of organic nitrogen were carried out with wild type *Trichoderma reesei* OM6a and RL-P37. The mutant RL-P37 secreted 4-5 times more total cellulase than the wild type QM6a. The specific productivities were 108 I.U./l/hr. for RL-P37 and 18 I.U./l/hr. for QM6a, indicating a much greater rate of enzyme production in RL-P37. When RL-P37 was tested, the specific activity of the total cellulase complex (FPA activity) and endoglucanase specific activity showed a two-fold increase over certain other strains of *Trichoderma reesei*, namely OM6a (wild type), QM9414, NG14, MCG77, and L-27 (strains of improved cellulase activity as compared to the wild type). (See Table 1.)

An example of the procedure used to characterize RL-P37 involves growing RL-P37 on either potato dextrose agar (Difco) or a medium containing Vogels salts (see H. J. Vogel, "A Convenient Growth Medium for Neurospora 5 (medium N)," *Microb. Genet. Bull.* 13: 42-43 (1956)), 0.1% proteose peptone (Difco), 1% cellulose (Solka floc. BW200, Brown Co., Berlin, N.H.), and 1.5% agar.

Then fermentations were carried out by growing the seed cultures (250 ml.) in the medium of Tangnu modified by replacing 1% cellulose with 1% lactose. (See S. K. Tangnu, H. W. Blanch, and C. R. Wilke, "Enhanced Production of Cellulose, Hemi-Cellulose, and $\beta$-glucosidose by *Trichoderma reesei* (RUT-30)." *Biotechnol. and Bioeng.* 23: 1837-49 (1981)). The seed flasks were inoculated with a spore suspension ($2-4\times10^7$), which had been passed through sterile glass wool to remove the mycelia. The flasks were incubated with shaking at room temperature. After 48 hours, seed flasks were used as an inoculum in (10% v/v) for fermentation.

The fermentation medium (4-10) was that of Tangnu et al and contained 5% cellulose (Solka Floc BW 200, Brown Co.) and either 0.29% proteose peptone (Difco) or 1.02% cornsteep liquor (Sigma). The pH was maintained at 5.0 with the automatic addition of either 14.8M or 7.4M ammonium hydroxide and the temperature was maintained at 29° C. Samples were filtered through micracloth (Calbiochem) to remove the mycelia and the culture filtrates that were used for enzyme analysis.

The cellulase enzymes were analyzed according to the methods of Mandels et al (See M. Mandels, R. Andreotti, and C. Roche, "Measurement of Saccharifying Cellulase," E. L. Gader, M. H. Mandels, E. T. Reese and L. A. Spano, eds., *Enzymatic Conversion of Cellulosic Materials: Technology and Applications*, John Wiley and Sons (New York) (1976)), in 0.05M citrate buffer, pH 4.8, at 50° C. Reducing sugars were quantified by the dinitrosalicylic acid method (see G. L. Miller, "Use of Dinitrosalicylic Acid Reagent for Determination of Reducing Sugar," *Anal. Chem.* 31: 426-28 (1969)). In the case of the filter paper assay, the enzyme unit was calculated at 4% degradation of the substrate (2 mg. reducing sugar) in order to measure solubilization of both crystalline and amorphous cellulose. Cellobiase activity was measured employing either cellobiose or p-nitrophenyl β-D-glucoside (Sigma) as substrates. When cellobiose was the substrate, glucose was measured enzymatically by the glucose oxidase/peroxidase assay. Acid insoluble protein in the culture filtrates was determined according to Lowry et al, with bovine serum albumin as a standard. (See O. H. Lowry, N. J. Rosebrough, A. J. Farr, and R. J. Randall, "Protein Measurements with the Folin Phenol Reagent," *J. Biol. Chem.* 198: 265-75 (1951). All cellulase units were expressed as moles of glucose equivalents per minute per ml. of culture filtrate. Protease activity was estimated with either azocasein (Sigma) or azocoll (calbiochem) as substrate at 37° C.

Culture filtrates were prepared for isoelectric focusing by concentration (2 to 10 times) and dialysis through a PM-10 membrane (Amicon). Slab gels (14cm.×16 cm.×0.075 cm.) contained 5.84% acrylamide (Aldrich), 0.16% N, N-methylene bis-acrylamide (Aldrich), 2% ampholytes (pH range 4 to 6.5 LKB), 5% glycerol, 0.2% N,N,N,N tetramethylene diamine (BioRad), and 0.075% ammonium persulfate. Samples containing 150 to 300 μg of protein were isoelectrically focused for 18 hours at 100 volts followed by 2 hours at 800 volts. Gels were fixed in 10% trichloroacetic acid overnight followed by an 8 hour soak in 25% isopropanol/10% acetic acid. After these treatments, gels were either stained for protein with Coomassie blue or silver (see J. H. Morrissey, "Silver Stain for Proteins in Polyacrylamide Gels: A Modified Procedure with Enhanced Uniform Sensitivity," *Anal. Biochem* 117: 307-10 (1981)), or for glycoprotein with Schiffs reagent (see G. Dubray and G. Bezard, "A Highly Sensitive Periodic Acid-Silver Stain for 1,2 Diol Groups of Glycoproteins and Polysaccharides in Polyacrylamide Gels," *Anal. Biochem* 119: 325-29 (1982)).

For localization of enzyme activities after isoelectric focusing, modifications of the method of Schulein et al were employed. (See M. Schulein, H. E. Schiff, P. Schneider & C. Dambmann, "Immuno-electrophoretic Characterization of Cellulolytic Enzymes from *Trichoderma reesei*," T. K. Ghose, ed., *Bioconversion and Biochemical Engineering*, 97, IIT, Delhi (1981)). For localization of endoglucanase activity gels were overlayed with a solution containing 1% agarose and 1% carboxymethyl cellulose (4M, Hercules, Inc., Wilmington, Del.) in 0.05M citrate buffer (pH 4.8). The gel was incubated at 50° C. for 20 minutes and undigested carboxymethyl cellulose was stained with Congo red. (See R. M. Teather and P. J. Wood, "Use of Congo Red-Polysaccharide Interactions in Enumeration and Characterization of Cellulolytic Bacteria From the Bovine Rumen." *Appl. and Envir. Microbiol.* 43: 777-80 (1982)). For localization of enzymes able to digest acid swollen cellulose gels were overlayered with a solution containing 1% agarose and 1% phosphoric acid swollen cellulose prepared by the method of Tansey (see M. R. Tansey, "Agar-Diffusion Assay of Cellulolytic Ability of Thermophilic Fungi," *Arch. Mikrobiol.* 77:1-11 (1971)), and incubated at 50° C. until bands of clearing appeared.

These results show the cellulase of RL-P37 to have a distinctive pattern of extra-cellular proteins and as previously indicated to have a higher specific activity and higher productivity as compared to, e.g., its immediate parent, NG14, its wild strain parent, QM6a, and to cellulase of selected other mutants. (See Table 1.)

TABLE 1

Specific Activity and Productivity of Cellulases Produced During Controlled Fermentation by *Trichoderma reesei* QM6a and its Mutant RL-P37

| Strain | Nitrogen Supplement | Specific Activity FPA, I.U./mg. | Specific Activity Endoglucanase I.U./mg. Protein | Productivity FPA I.U./1/hr. |
|---|---|---|---|---|
| QM6a[1] | peptone | 0.7 | 12.0 | 15 |
| QM6a[3] | cornsteep liquor | 0.52 | 27.5 | 18 |
| RL-P37[3] | peptone | 1.14 | 44.7 | 41 |
| RL-P37[3] | cornsteep liquor | 1.33 | 46.8 | 108 |
| QM9414[1] | peptone | 0.73 | 8.0 | 30 |
| MCG77[1] | peptone | 0.66 | 6.4 | 33 |
| L-27[2] | peptone | 0.82 | 3.6 | 94 |
| NG14[1] | peptone | 0.7 | 6.3 | 45 |

[1]Data from: D. Y. Ryu and M. Mandels, "Cellulases: Biosynthesis and Applications", Enzyme Microb. Technol. 2: 91-102 (1980).
[2]Data from S. P. Shoemaker, J. C. Raymond and R. Bruner, "Cellulases: Diversity Amongst Improved Trichoderma Strains", A. Hollaender, ed., Trends in the Biology of Fermentations for Fuels and Chemicals, p. 89 Plenum Press, New York (1981).
[3]Test results of present invention.

I claim:

1. A biologically pure culture of *Trichoderma reesei* RL-P37.

2. A process utilizing *Trichoderma reesei* RL-P37 for the production of an extracellular glycoprotein enzyme, from the group consisting of carbohydrases, proteases, lipases, and nucleases, said process comprising culturing the microbial strain RL-P37 and permitting said cultured strain to secrete said enzyme.

3. A process utilizing *Trichoderma reesei* RL-P37 for the production of an extracellular glycoprotein enzyme, from the group consisting of cellulases, laminarinases, amylase, xylanases and pectinases, said process comprising culturing the microbial strain RL-P37 and permitting said cultured strain to secrete said enzyme.

4. A process utilizing *Trichoderma reesei* RL-P37 for the production of at least one cellulolytic enzyme, from the group consisting of exocellobiohydrolase, endoglucanase, β-glucosidase, and cellobiase, said process comprising culturing the microbial strain, RL-P37, on a carbon-containing inducing substrate and then permitting said cultured strain in the presence of said inducing substrate to secrete said enzyme.

5. The process of claim 4, wherein said carbon-containing inducing substrate is one or more members of the group consisting of cellulose, cellulose derivatives, steam expanded cellulose, β-linked glucosides, cellobiose, wood, wood products, paper, cellulosic agricultural products, cellobiose octaacetate, cellulose mono-, di- or triacetate, carboxymethyl cellulose, hydroxyethyl cellulose, carboxymethyl hydroxyethyl cellulose, esculin or hemicellulosic material.

6. The process of claim 5, wherein said substrate is steam exploded wood.

7. A process for treating a cellulosic mass comprising:
   (1) producing cellulolytic enzymes by a process as recited in claim 5;
   (2) contacting said secreted cellulolytic enzymes from step (1) with a cellulosic mass to be treated until the glucan content thereof is substantially hydrolyzed.

8. A process as recited in claim 7, wherein said substrate and said cellulosic mass is steam exploded wood.

9. A process as recited in any one of claims 2 through 8, wherein said strain is first cultured at a temperature of about 37° C. and then said cultured strain is permitted to secrete said enzyme at an optimal temperature for said secretion.

10. A process as recited in any one of claims 4 though 8 wherein said strain is first cultured at about 37° C. and then said cultured strain is permitted to secrete said enzyme at about 28° C.

* * * * *